United States Patent [19]
Schwartz et al.

[11] Patent Number: 5,474,073
[45] Date of Patent: Dec. 12, 1995

[54] ULTRASONIC DIAGNOSTIC SCANNING FOR THREE DIMENSIONAL DISPLAY

[75] Inventors: Gary A. Schwartz, Seattle; Patrick R. Pesque, Bothell; Jens U. Quistgaard, Seattle, all of Wash.

[73] Assignee: Advanced Technology Laboratories, Inc., Bothell, Wash.

[21] Appl. No.: 343,811

[22] Filed: Nov. 22, 1994

[51] Int. Cl.⁶ .................................................. A61B 8/00
[52] U.S. Cl. .................. 128/661.10; 128/916; 73/861.25
[58] Field of Search ......................... 128/660.07, 661.08, 128/661.09, 661.10, 916; 73/861.25

[56] References Cited

U.S. PATENT DOCUMENTS

| | | | |
|---|---|---|---|
| 5,159,931 | 11/1992 | Pini | 128/660.07 |
| 5,282,471 | 2/1994 | Sato | 128/660.07 |
| 5,295,486 | 3/1994 | Wollschlager et al. | 128/661.01 |
| 5,315,512 | 5/1994 | Roth | 364/413.25 |
| 5,329,929 | 7/1994 | Sato | 128/660.65 |

OTHER PUBLICATIONS

Three-Dimensional Reconstruction of Echocardiograms Based on Orthogonal Sections, S. Tamura et al., Pattern Recog., (1985) p. 115.
Multidimensional Ultrasonic Imaging for Cardiology, H. A. McCann et al. Proc. IEEE, v. 76, No. 9, (Sep. 1988) pp. 1063–1073.

Primary Examiner—George Manuel
Attorney, Agent, or Firm—W. Brinton Yorks, Jr.

[57] ABSTRACT

An ultrasonic diagnostic system and scanning technique are described for producing three dimensional ultrasonic image displays utilizing power Doppler signal information. In a preferred embodiment the power Doppler signal information is displayed in the absence of structural (B mode) information to reduce image clutter and provide three dimensional image segmentation. An ultrasonic scanning technique is presented for acquiring diagnostic three dimensional ultrasonic images of power Doppler intensity through manual hand scanning of a patient, without the need for specially fabricated scanning mechanisms or devices.

18 Claims, 6 Drawing Sheets

ULTRASONIC DIAGNOSTIC SCANNING FOR THREE DIMENSIONAL DISPLAY

This invention relates to improvements in ultrasonic diagnostic imaging techniques, and in particular to ultrasonic scanning of the body to acquire Doppler information for presentation in a three dimensional image format.

Various methods and devices have been proposed for ultrasonically scanning a volume within a subject for three dimensional analysis and display. Many of these techniques involve the scanning of a number of spatially adjacent image planes. The ultrasonic information from these associated planes can be analyzed and displayed on the basis of spatial coordinates of the data within a plane, and on the basis of the spatial relationship of each plane to the others. The information can be displayed in a three dimensional image format such as a perspective view of the volume being imaged.

A number of scanning techniques utilizing specially devised scanning devices have been proposed for acquiring these spatially related image planes. The article "Three-Dimensional Reconstruction of Echocardiograms Based On Orthogonal Sections," by S. Tamura et al., *Pattern Recognition*, vol. 18, no. 2, pp 115–24 (1985) discusses three such devices: a guide rail to guide an ultrasonic probe while acquiring parallel image planes; a jointed arm in which sensors in the arm joints provide spatial coordinates for the transducer; and rotation of a transducer about the cardiac long axis. A rotating transducer probe for the latter purpose is shown and described in "Multidimensional Ultrasonic Imaging for Cardiology," by H. McCann et al., *Proceedings of the IEEE*, vol. 76, no. 9, pp 1063–73 (Sept. 1988). It would be preferable, however, to be able to acquire multiple image planes for three dimensional presentation without the need for special scanning devices or apparatus.

Ultrasonic images are subject to image artifacts arising from a number of sources such as reverberation, multipath echoes, and coherent wave interference. These artifacts will manifest themselves in various ways in the image which can be broadly described as image clutter. The image clutter becomes particularly troublesome when images are presented in a three dimensional format, as the three dimensional clutter can interfere with and obscure pathology which the clinician is attempting to diagnose. Accordingly it would be desirable to provide ultrasonic image information in a format in which clutter does not significantly impair the pathology being viewed.

In accordance with the principles of the present invention the present inventors have addressed this problem of obscuring clutter through the use of ultrasonic Doppler information signals. Doppler information has been used to image the body in two distinct ways. One Doppler imaging technique is commonly referred to as color Doppler velocity imaging. As is well known, this technique involves the acquisition of Doppler data at different locations called sample volumes over the image plane of an ultrasonic image. The Doppler data is acquired over time and used to estimate the Doppler phase shift or frequency at each discrete sample volume. The Doppler phase shift or frequency corresponds to the velocity of tissue motion or fluid flow in vessels within the body, with the polarity of the shift indicating direction of motion or flow. This information is color coded in accordance with the magnitude of the shift (velocity) and its polarity, and overlaid over a structural image of the tissue in the image plane to define the structure of the moving organs or vessels in which fluids are flowing. The colors in the image thereby provide an indication of the speed of blood flow and its direction in the heart and blood vessels, for instance.

A second Doppler technique is known as color power Doppler. This technique is unconcerned with estimations of the velocity of motion or fluid flow. Rather, it focuses simply on the intensity of the received signals which exhibit a Doppler shift. This Doppler signal intensity can be measured at each sample volume in an image plane and displayed in a color variation. Unlike color Doppler velocity imaging, color power Doppler does not present the problems of directionality determination, aliasing, and low sensitivity which are characteristic of velocity imaging. Color power Doppler simply displays the Doppler signal intensity at a sample volume in a coded color. Like color Doppler velocity imaging, the color power Doppler display is overlaid with a structural B mode image to define the organ or tissue structure in which motion is occurring. Since the value at each sample volume can be averaged over time or based upon a peak value, and is not subject to the constant changes of velocity and direction which are characteristic of the pulsatility of Doppler velocity signals, the color power Doppler display can be presented as a more stable display of motion or flow conditions in the body.

In accordance with the principles of the present invention, a three dimensional ultrasonic display technique is provided which utilizes power Doppler signal information. The present inventors have utilized power Doppler images in an unconventional way, which is in the absence of structural (B mode) information. The present inventors have discovered that utilizing power Doppler information alone in a three dimensional display eliminates the substantial clutter contribution of the structural information signals, eliminates pulsatility variation, provides excellent sensitivity to low energy flow signals, reduces Doppler angle effects, and provides a segmentation of the flow or motion characteristics in the three dimensional image. The present inventors also present a technique for acquiring diagnostic three dimensional ultrasonic images through manual hand scanning of a patient, without the need for specially fabricated scanning mechanisms or devices.

Figure 1:
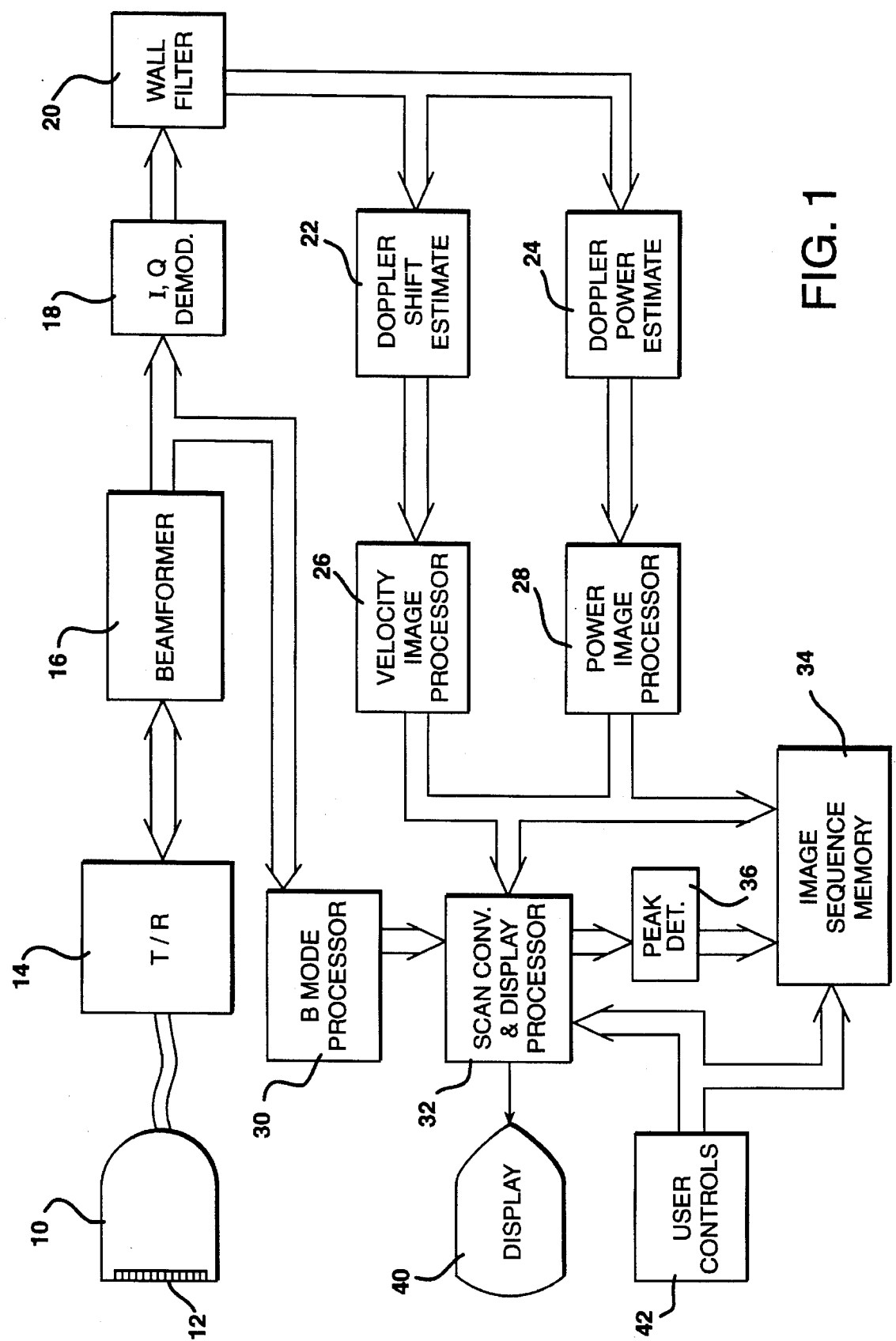
FIG. 1 is a block diagram of an ultrasonic diagnostic imaging system constructed in accordance with the principles of the present invention.

Referring first to FIG. 1, a block diagram of an ultrasonic diagnostic imaging system constructed in accordance with the principles of the present invention is shown. An ultrasonic probe 10 includes a multielement transducer 12 which transmits waves of ultrasonic energy into the body of a patient and receives ultrasonic echoes returning from structures in the body. In the case of ultrasonic wave transmission for Doppler interrogation of the body, it is the echoes returning from moving tissue, blood and other fluids in the body that are of interest. The ultrasonic probe 10 is connected to a transmitter/receiver 14 which alternately pulses individual elements of the transducer to shape and steer an ultrasonic beam, and receives, amplifies and digitizes echo signals received by the transducer elements following each pulse transmission.

The transmitter/receiver 14 is coupled to a beamformer 16 which controls the times of activation of specific elements of the transducer 12 by the transmitter/receiver. This timing enables the transducer 12 to transmit a shaped and focused ultrasound beam in a desired direction. The beamformer 16 also receives the digitized echo signals produced by the transmitter/receiver during echo reception and appropriately delays and sums them to form coherent echo signals.

The echo signals produced by the beamformer 16 are coupled to a B mode processor 30 and an I,Q demodulator 18. The B mode processor processes the amplitude information of the echo signals on a spatial basis for the formation of a structural image of the tissue in the area of the patient being scanned. The I,Q demodulator 18 demodulates the received echo signals into quadrature components for Doppler processing. The I,Q components are filtered by a wall filter 20 to remove low frequency artifacts stemming from the movement of vessel walls in applications where it is only the motion of flowing fluids such as blood that is of interest. The filtered I,Q components are then applied to a Doppler shift estimation processor 22 and a Doppler power estimation processor 24.

The Doppler shift estimation processor 22 operates in the conventional manner to estimate a Doppler phase or frequency shift from the I,Q components at each sample volume location of the image field. The Doppler shift estimation processor operates on a number of signal samples resulting from the interrogation of each sample volume location by an ensemble of Doppler interrogation pulses. The sample volume values are applied to a velocity image processor 26 which maps the values to color values for display. The color values are applied to a scan converter and display processor 32 which spatially arranges the color values in the desired image format. The color values are displayed as pixels on a display 40, wherein each color represents a particular velocity of flow in a particular direction at that pixel location. The color flow velocity information is overlaid with a structural image of the interior of the body utilizing the structural information provided by the B mode processor 30. This compound image shows both the direction and velocity of blood flow, as well as the structure of the vessels or organs which contain the flowing blood.

In accordance with the principles of the present invention the Doppler system of FIG. 1 also includes a power Doppler imaging capability. The power Doppler components include a Doppler power estimation processor 24 which estimates the Doppler signal power magnitude from the I,Q signal components at each sample volume location using the expression $(I^2+Q^2)^{1/2}$. The Doppler power estimates at each location can be processed and displayed in real time or can be averaged with earlier acquired power estimates for each sample volume location. In a preferred embodiment, each sample volume location is interrogated by a number of pulses and the estimation processor 24 utilizes the signals obtained from all interrogations in the estimations of Doppler power at the sample volume locations. These Doppler power estimates are mapped to display intensity or color values by a power image processor 28. The display values with their spatial coordinates are stored in separate planar images in an image sequence memory 34 and are also applied to the scan converter and display processor 32 which spatially arranges the Doppler power display values in the desired image format, e.g., sector or rectangular. The two dimensional Doppler power images may then be displayed on a display 40 or recalled from the image sequence memory 34 for three dimensional processing using a peak detector 36 for maximum Doppler power intensity detection as discussed below. User operation of the system of FIG. 1 is effected through various user controls 42 which enable the user to select the type of imaging to be performed, i.e., B mode, color velocity Doppler or Doppler power imaging, and to store and retrieve images from the image sequence memory 34 for three dimensional display, for example.

Figure 2:
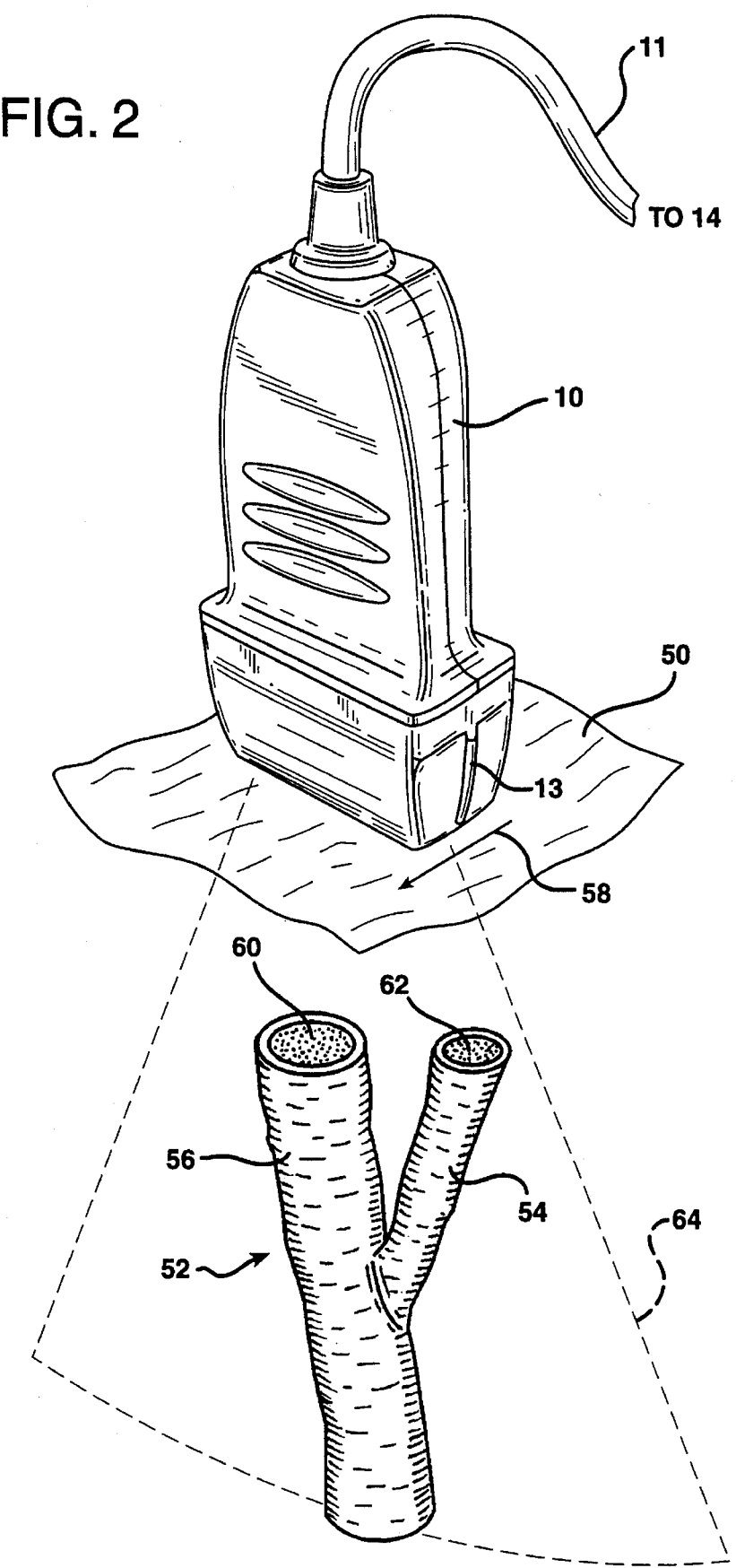
FIG. 2 illustrates the manual scanning of a bifurcation in the body of a patient.
Figure 3C:
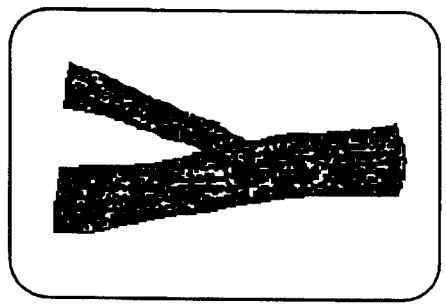
FIGS. 3a–3e illustrate a sequence of two dimensional Doppler power images acquired from the bifurcation of FIG. 2.

FIG. 2 illustrates the use of the ultrasonic probe 10 to manually acquire a sequence of image planes for three dimensional display. A portion of the probe cable 11 leading to the transmitter/receiver of the ultrasound system is shown at the top of the probe. The transducer aperture of the probe 10 is in contact with the skin of the patient over the region of the body which is to be scanned. The skin of the patient is represented by a layer 50 in the drawing. In this example the region of the patient being scanned includes a blood vessel bifurcation 52 having a small vessel 54 branching out from a larger vessel 56. Blood is flowing inside the structural walls of the vessels as indicated at 60 and 62.

The bifurcation 52 may be scanned by rocking or fanning the probe 10 while it is in contact with the patient. In a preferred technique the probe aperture slides over the skin 50 as indicated by arrow 58 to scan the bifurcation region with a plurality of substantially parallel image planes. One such image plane 64, here shown as a sector, is seen projecting from the transducer aperture of the probe. The relation of the image plane 64 to the probe is denoted by an image plane marker 13 on the side of the probe case. The marker 13 is in the same plane as the image plane 64, and denotes the upper left side of the image in its uninverted display orientation.

In accordance with the present invention, the ultrasound system acquires and processes power Doppler information from a plurality of image planes as the probe slides over the bifurcation region of the patient as indicated by the arrow 58. The duration of such a scan can typically last about ten to twenty seconds, during which time 100 to 200 image planes of power Doppler information are acquired, processed and stored in the image sequence memory 34. This image information is processed to detect and record the maximum Doppler intensity at a number of different viewing angles over a range of such viewing angles as discussed below.

Figure 4:
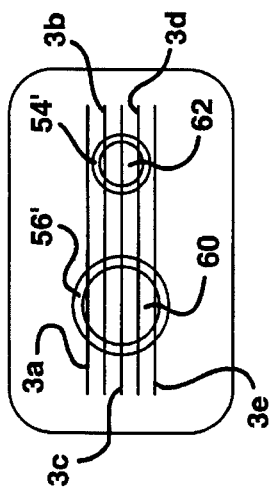
FIG. 4 illustrates the relation of the image planes of FIGS. 3a–3e to the structure of the bifurcation of FIG. 2.
Figure 3B:
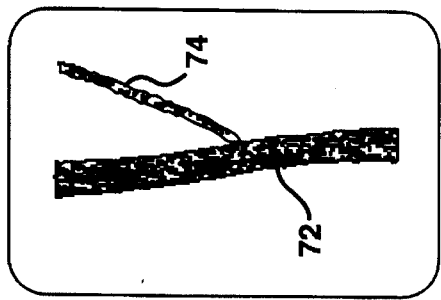
Figure 3E:
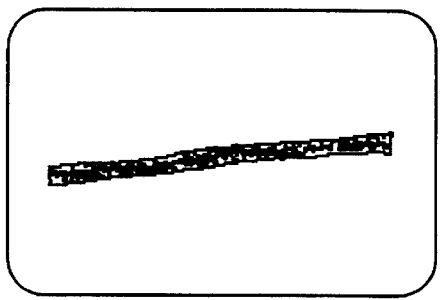
Figure 3A:
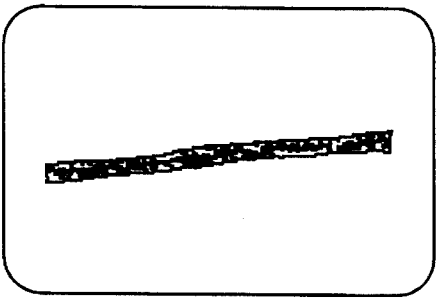
Figure 3D:
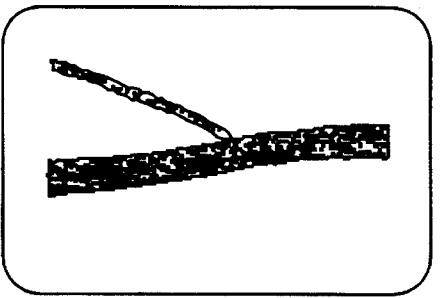

FIGS. 3a–3e shows a five image plane sequence which illustrates the principles of the power Doppler three dimensional imaging technique of the present invention. The five image planes of the sequence are referenced to the structure of the bifurcation 52 in FIG. 4, which is a view of the top of the two vessels. FIG. 3a is a power Doppler image taken along plane 3a of FIG. 4, which is seen to intersect the upper edge of the blood flow of the large vessel 56, just inside the vessel wall 56'. In FIG. 3b the image plane intersects a greater cross section 72 of the blood flow of the large vessel 56, and the edge 74 of the blood flow of the small vessel 54, just inside the vessel wall 54' as plane 3b of FIG. 4 shows. The image plane of FIG. 3c intersects the centers of both vessel as is seen by plane 3c in FIG. 4. In FIG. 3d the image plane moves down to a lesser cross section of both vessels and the plane 3e of FIG. 3e intersects only the peripheral blood flow in the large vessel 56.

Figure 5B:
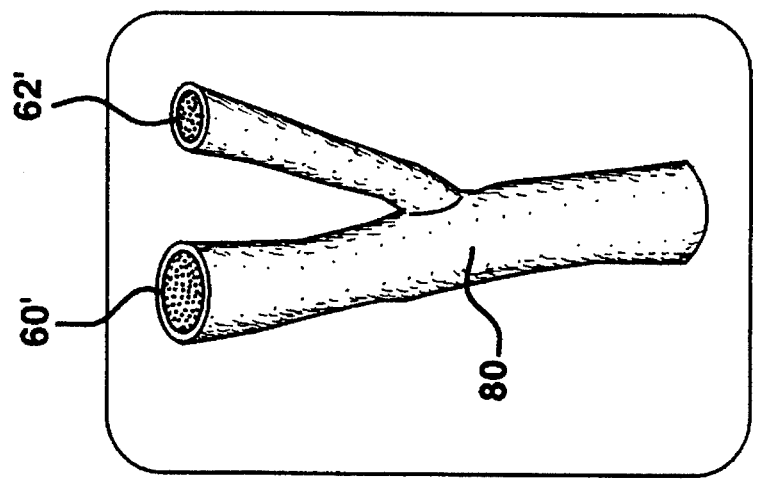
FIGS. 5a and 5b are a comparison of the bifurcation of FIG. 2 to a three dimensional Doppler power display of the blood flow of the bifurcation.
Figure 5A:
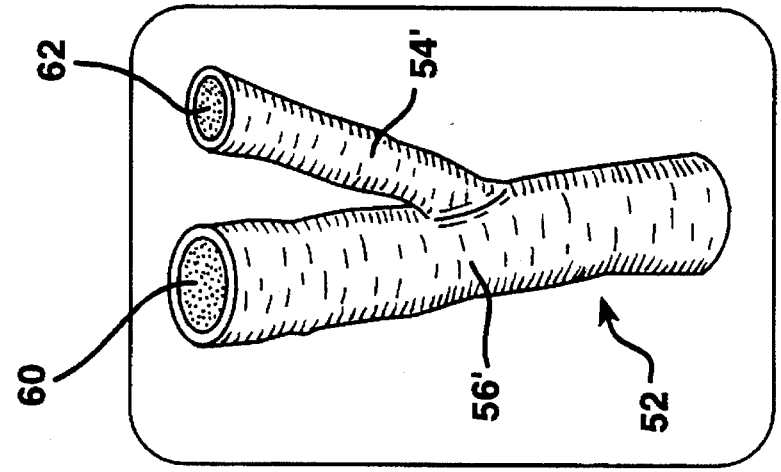

The images of FIGS. 3a–3e are processed and presented together in a three dimensional presentation as illustrated in FIG. 5b. The three dimensional image is seen to comprise the power Doppler information without any structural image overlay. This is clearly seen by comparing the three dimensional power Doppler image 80 of FIG. 5b with the similarly scaled rendering of the bifurcation 52 in FIG. 5a. The rendering of FIG. 5a is seen to include the structure of the vessel walls 54' and 56' which contain flowing blood indicated at 60 and 62. The power Doppler image 80, resulting from the Doppler detected movement of the flowing blood, is displayed without any B mode structure of the vessel walls 54' and 56'. It has been found that omitting the vessel walls from the three dimensional display does not diminish the effectiveness of the display, as the continuity of the blood flow intensity serves to define the paths in which blood is flowing. In addition, the absence of B mode echos eliminates considerable structural echo clutter from the image. The image is clearly segmented by the flow selectivity, and the smoothly varying stability and sensitivity of the maximum intensity power Doppler information.

Figure 8:
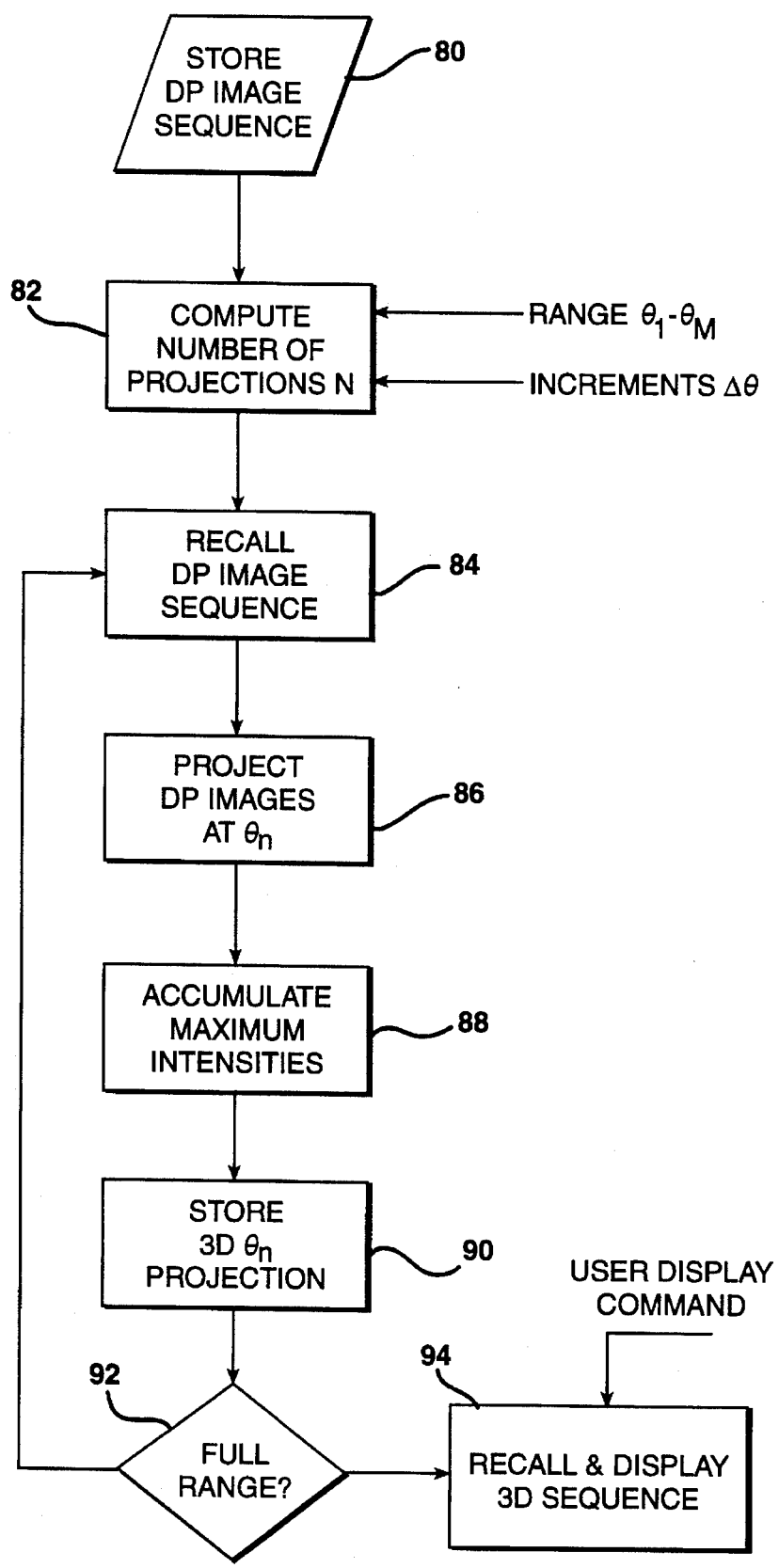
FIG. 8 is a flow chart used to explain the preferred technique for processing Doppler power images for three dimensional display.

FIG. 8 is a flowchart illustrating a preferred technique for processing a sequence of planar Doppler power images for real time three dimensional display. As described above, the Doppler power display values with their spatial coordinates are stored in a sequence of planar images in the image sequence memory 34, as shown by step 80 in FIG. 8. The images of FIGS. 3a–3e are illustrative of such a two dimensional image sequence. In step 82 the process receives processing parameters provided by the user controls. One parameter is the range of viewing angles, $\theta_1$-$\theta_M$, over which the three dimensional presentation is to be viewed. The other parameter is the increment $\Delta\theta$ between each viewing angle in the range. For instance the user could input a range of viewing angles of +60° to −60°, referenced to a line of view in a plane which is normal to the plane of the first image in the sequence, and a range increment of 1°. From these inputs the number of three dimensional projections needed is computed in step 82. In this example 121 projections are needed to display a 120° range span in one degree increments.

The process now begins to form the necessary sequence of 121 maximum intensity projections. In step 84 the planar Doppler power images are recalled from the image sequence memory for sequential processing by the scan converter and display processor 32. In step 86 each planar image is rotated to one of the viewing angles $\theta_n$, then projected back to the viewing plane. In step 88 the pixels of the projected planar images are accumulated on a maximum intensity basis. Each projected planar image is overlaid over the previously accumulated projected images but in a transposed location in the image plane which is a function of the viewing angle and the interplane spacing: the greater the viewing angle, the greater the transposition displacement from one image to the next. The display pixels chosen from the accumulated images are the maximum intensity pixels taken at each point in the image planes from all of the overlaid pixels accumulated at each point in the image. This effectively presents the maximum intensity of Doppler power seen by the viewer along every viewing line between the viewer and the three dimensional image. In a preferred embodiment the relocation of image points after rotation about the y axis, projection and transposition may be expressed as:

$$\begin{bmatrix} x' \\ y' \end{bmatrix} = \begin{bmatrix} x\cos(\theta) \\ y \end{bmatrix} + \begin{bmatrix} z\sin(\theta) \\ 0 \end{bmatrix}$$

and the relocation of image points after rotation about the x axis, projection and transposition may be expressed as:

$$\begin{bmatrix} x' \\ y' \end{bmatrix} = \begin{bmatrix} x \\ y\cos(\theta) \end{bmatrix} - \begin{bmatrix} 0 \\ z\sin(\theta) \end{bmatrix}$$

where $\theta$ is the angle of rotation, (x, y, z) are the coordinates of a point to be relocated, and (x', y') are the coordinates of a point in the viewing plane after relocation.

After all of the planar images have been rotated, projected, transposed, overlaid, and the maximum intensities at each pixel chosen, the resulting three dimensional image for the viewing angle $\theta_n$ is stored in the image sequence memory 34 as a brightness modulated monochrome image in a three dimensional image sequence. In step 92 the process returns to step 84 and proceeds through steps 84–92 until the full three dimensional image sequence has been stored in memory. In the present example this is a sequence of 121 three dimensional images over the range of +60° to −60°.

The stored three dimensional sequence is now available for recall and display in step 94 upon command of the user. As the sequence is recalled and displayed in real time, the user sees a three dimensional presentation of the motion or fluid flow occurring in the volumetric region over which the planar images were acquired. The volumetric region is viewed three dimensionally as if the user were moving around the region and viewing the motion or flow from changing viewing angles. In this particular example the user has the impression of moving over a range of viewing angles spanning 120° around the volumetric region. The viewer can sweep back and forth through the sequence, giving the impression of moving around the volumetric region in two directions.

Figure 6A:
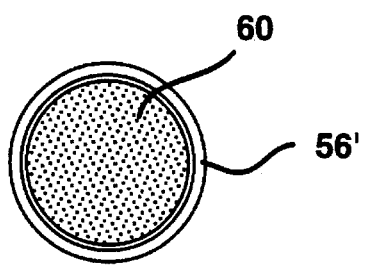
FIGS. 6a–6d illustrates the three dimensional relationship of manually acquired two dimensional image planes.
Figure 6B:
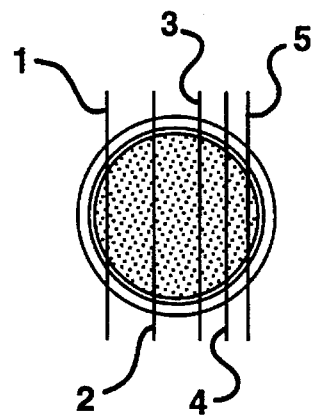

FIGS. 6a–6d illustrate the effects of nonuniform spacing of image planes which can arise from manual image plane scanning. FIG. 6a is a top view of the large vessel 56, showing the blood flow 60 surrounded by the vessel wall 56' for reference. FIG. 6b shows another sequence of five image planes taken across the vessel but unlike the sequence of FIG. 4, these image planes are unevenly spaced. Image planes 1 and 2 are seen to be more widely spaced than the closer spacing of image planes 4 and 5. Such a spacing will result for instance when the probe slides faster when acquiring image planes 1 and 2 and slows down as it approaches the positions of image planes 4 and 5. This sequence is acquired by manually sliding the probe from left to right at a progressively slower speed across the skin above the vessel 56.

Figure 6C:
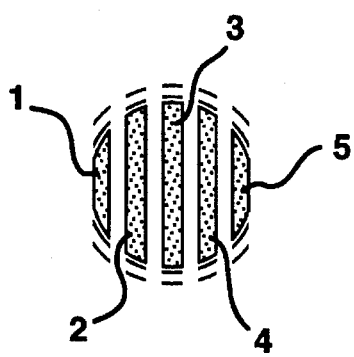
Figure 6D:
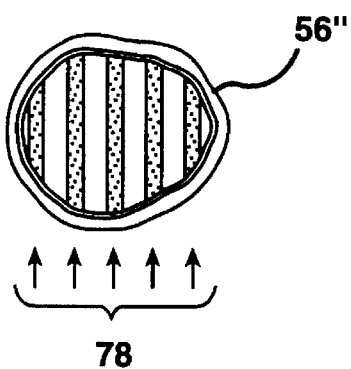

In a constructed embodiment of the present invention the image planes are assumed to be evenly spaced across the imaged volume and are processed and displayed accordingly. FIG. 6c shows the five image planes of FIG. 6b from above when they are evenly spaced for display. The result of this spacing is more readily seen in FIG. 6d, in which the border of the blood flow and the vessel wall 56'' have been reconnected for ease of illustration. The arrows at 78 illustrate the uniform image plane spacing, which is slightly less than the spacing of image planes 1 and 2 in FIG. 6b and slightly greater than the spacing of image planes 5 and 6 in that drawing. The effect is to give the cross sectional area of the blood flow a slightly oblong appearance in which the left side of the flow area is compressed and the right side extended in relation to the actual proportions of the blood flow area.

The present inventors have observed that this distortion of the aspect ratio of the three dimensional image does not noticeably detract from the effect of the overall three dimensional display. Even with such aspect distortion the three dimensional image continues to show the relative paths and orientations of blood vessels and the continuity or stenosis of flow in vessels in a manner not achieved by two dimensional presentations. The continuity of flow paths and display effectiveness is enhanced by displaying the Doppler power on the basis of the maximum signal intensity. When the image planes are acquired from a range of acquisition angles the use of the maximum intensity display has the effect of diminishing sensitivity variation resulting from Doppler angle effects. The image planes may be concurrently displayed in the form of a surface rendering or a transparency of the blood flow information, but a preferred presentation is a monochrome display of the varying brightness of the maximum intensity pixels of the combined images of a volumetric region as described above. The flow and perfusion of the blood supply in an organ such as a kidney is more completely displayed with a three dimensional power Doppler image than can be accomplished with a two dimensional presentation. The technique is well suited for assessing the success of organ transplants, for instance.

Figure 7:
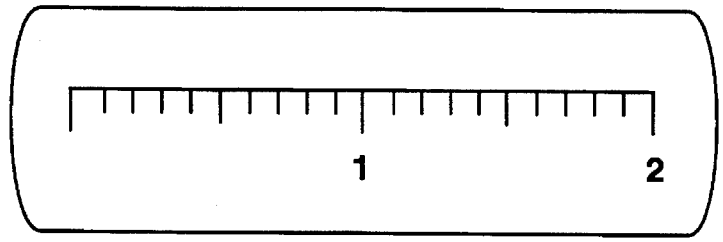
FIG. 7 illustrates a scanning aid for manually acquiring uniformly spaced image planes.

Simple aids may be provided to improve the accuracy of manual three dimensional scanning if desired. One such aid is shown in FIG. 7, and comprises a ruler scale printed on a clear strip of surgical tape. The tape is applied to the skin of the patient adjacent to the probe, and the probe is moved along the scale with the marker 13 on the probe used as a reference. Image planes can be acquired at each marker on the scale, or the scale can be traversed in a given time such as twenty seconds. Other aids may also be supplied by the ultrasound system such as audible signals or lights telling the user when to start and stop movement of the probe, and when the moving probe should be passing each marker on the scale.

The imaging techniques of the present invention including particularly that of FIG. 8 can be applied to a sequence of planar images acquired with position sensing of the image planes for display of anatomically precise images. An advantageous Doppler technique for sensing the positions of the image planes and lines in each plane in relation to each other is described in U.S. Pat. No. 5,127,409. When the positions of the image planes or lines are known in relation to each other the three dimensional processor no longer has to assume uniform spacing between two dimensional planes, but can utilize the measured spacing between three dimensional display elements to form more geometrically accurate three dimensional images.

What is claimed is:

1. A method for producing three dimensional ultrasonic images of the interior of a body comprising the steps of:

transmitting ultrasonic waves over a volumetric region of the interior of the body;

receiving ultrasonic Doppler information signals from spatial locations within said region;

processing said ultrasonic Doppler information signals to determine the Doppler power intensity received from said locations within said region; and displaying said Doppler power intensity on a spatial basis in a three dimensional presentation.

2. The method of claim 1, wherein said step of processing comprises the step of processing said ultrasonic Doppler information signals to determine the maximum Doppler power intensity received from said locations within said region; and wherein said step of displaying comprises the step of displaying said maximum Doppler power intensity of said locations on a spatial basis in a three dimensional presentation.

3. The method of claim 2, wherein said step of transmitting comprises the step of transmitting ultrasonic waves over a series of planar regions of a volumetric region of the interior of the body; and wherein said step of receiving comprises the step of receiving ultrasonic Doppler information signals from spatial locations within said planar regions.

4. The method of claim 3, wherein said step of processing comprises the step of processing said ultrasonic Doppler information signals in spatially related image planes to determine the Doppler power intensity received from said locations within each of said image planes; and wherein the step of displaying comprises the step of concurrently displaying said Doppler power intensity of a plurality of said image planes on a spatial basis in a three dimensional presentation.

5. The method of claim 4, further comprising the step of identifying the maximum Doppler power intensity at each point in a combination of said spatially related image planes; and wherein the step of displaying comprises the step of displaying said identified maximum Doppler power intensities on a spatial basis in a three dimensional display.

6. The method of claim 1, wherein said step of displaying comprises the step of displaying said Doppler power intensity on a spatial basis in the absence of structural echo information signals in a three dimensional presentation.

7. The method of claim 1, further comprising the step of providing said transmitting and receiving steps by manually moving an ultrasonic transducer probe which is in contact with said body.

8. An ultrasonic diagnostic imaging system which is capable of providing three dimensional presentations of the interior of a body comprising:

an ultrasonic transducer probe for transmitting ultrasonic waves over a volumetric region of the interior of the body and for receiving ultrasonic Doppler information signals returned from spatial locations within said region;

a power Doppler processor responsive to said ultrasonic Doppler information signals for producing Doppler power intensity signals corresponding to said locations within said region;

an image processor for processing said Doppler power intensity signals for display in a three dimensional image presentation; and a display coupled to said image processor which displays said three dimensional image presentation.

9. The ultrasonic diagnostic imaging system of claim 8, wherein said image processor comprises means responsive to said Doppler power intensity signals for producing a maximum Doppler power intensity image of said region.

10. The ultrasonic diagnostic imaging system of claim 9, wherein said ultrasonic transducer probe comprises means for transmitting ultrasonic waves over a series of image planes of a volumetric region of the interior of the body and for receiving ultrasonic Doppler information signals returned from spatial locations within said image planes of said region.

11. The ultrasonic diagnostic imaging system of claim 10, wherein said image processor further comprises means for processing said Doppler power intensity signals in spatially related image planes to determine the Doppler power intensity corresponding to locations within each of said image planes; and wherein said display further comprises means for concurrently displaying said Doppler power intensity of a plurality of said image planes on a spatial basis in a three dimensional presentation.

12. The ultrasonic diagnostic imaging system of claim 11, further comprising a peak detector responsive to the Doppler power intensity determinations corresponding to locations within each of said image planes for identifying the maximum Doppler power intensity at points in a combination of a plurality of image planes; and wherein said display comprises means for displaying maximum Doppler power intensity images in the absence of concurrent display of tissue structure.

13. The ultrasonic diagnostic imaging system of claim 8, wherein said image processor further comprises means for processing said Doppler power intensity signals for display in the absence of tissue structure information signals in a three dimensional image presentation.

14. The ultrasonic diagnostic imaging system of claim 13, further comprising a peak detector responsive to said Doppler power intensity signals for identifying the maximum Doppler power intensity corresponding to said locations within said image planes.

15. The ultrasonic diagnostic imaging system of claim 14, wherein said ultrasonic transducer probe comprises a manual scanner which is manually moved in relation to said volumetric region to scan a sequence of spatially related image planes in said region.

16. An ultrasonic diagnostic imaging system which is capable of providing three dimensional presentations of a region of a body comprising:

an ultrasonic transducer probe for transmitting ultrasonic waves over a sequence of image planes of said region of the body and for receiving ultrasonic Doppler information signals returned from spatial locations within said image planes while said probe is manually incremented positionally in relation to said region;

a power Doppler processor responsive to said ultrasonic Doppler information signals for estimating the Doppler power corresponding to said locations within said image planes;

an image processor for processing said Doppler power estimates to produce a maximum Doppler power image for display in a three dimensional image presentation in the absence of non Doppler signal information; and a display responsive to the production of maximum Doppler power images which displays a sequence of said maximum Doppler power images in a three dimensional image presentation in the absence of a structural display of tissue.

17. The ultrasonic diagnostic imaging system of claim 16, wherein said image processor comprises means for accumulating said estimates of Doppler power of a plurality of said image planes to form a three dimensional display image of the maximum Doppler power intensity as seen by a viewer from a given viewing perspective.

18. The ultrasonic diagnostic imaging system of claim 17, further comprising an image sequence memory for storing said estimates of Doppler power in corresponding images and for storing a sequence maximum Doppler power images.

\* \* \* \* \*